US006352076B1

(12) United States Patent
French

(10) Patent No.: US 6,352,076 B1
(45) Date of Patent: Mar. 5, 2002

(54) ANESTHESIA INDUCTION CHAMBER FOR SMALL ANIMALS

(76) Inventor: Larry G. French, 13738 Coyote Hollow, Lot #2, San Antonio, TX (US) 78253

(*) Notice: Subject to any disclaimer, the term of this patent is extended or adjusted under 35 U.S.C. 154(b) by 97 days.

(21) Appl. No.: 09/606,077

(22) Filed: Jun. 29, 2000

Related U.S. Application Data

(60) Provisional application No. 60/141,858, filed on Jul. 1, 1999.

(51) Int. Cl.[7] .............................................. A61M 15/00

(52) U.S. Cl. ........................... 128/203.12; 128/202.12; 128/205.26; 119/420; 119/712

(58) Field of Search ....................... 128/203.12, 205.26, 128/200.24, 202.12; D24/224, 169; 119/712, 96, 417, 418, 420; 600/21, 22

(56) References Cited

U.S. PATENT DOCUMENTS

| | | | | | |
|---|---|---|---|---|---|
| 275,969 | A | | 4/1883 | Woodside | |
| 3,885,523 | A | | 5/1975 | Coleman | |
| 4,367,696 | A | | 1/1983 | Hamana | |
| 4,480,587 | A | | 11/1984 | Sedlacek | |
| 4,582,055 | A | * | 4/1986 | McDougal et al. | 128/202.12 |
| 4,690,100 | A | | 9/1987 | Thomas | |
| 4,699,088 | A | | 10/1987 | Murray et al. | |
| 4,788,934 | A | | 12/1988 | Fetter | |
| 4,941,431 | A | | 7/1990 | Anderson | |
| 5,010,845 | A | | 4/1991 | Azpurua et al. | |
| 5,090,357 | A | * | 2/1992 | Pucci | 119/5 |
| 5,134,969 | A | * | 8/1992 | Mason et al. | 119/17 |
| 5,190,879 | A | | 3/1993 | Wolfe et al. | |
| D399,609 | S | | 10/1998 | Allen et al. | |
| 5,865,144 | A | | 2/1999 | Semenuk | |

FOREIGN PATENT DOCUMENTS

| | | |
|---|---|---|
| GB | 1179551 | 1/1970 |
| GB | 2276088 | 9/1994 |

* cited by examiner

*Primary Examiner*—John G. Weiss
*Assistant Examiner*—Michael Mendoza
(74) *Attorney, Agent, or Firm*—Richard C. Litman

(57) ABSTRACT

An anesthesia induction chamber for small animals having a chamber defined by a bottom wall, a pair of opposing side walls, a front end wall, a rear door mounted on a hinge, and a top cover attached to a side wall by an elongated piano hinge. The walls, rear door and top cover are impermeable to gases. The front end wall has a gas inlet port to which a gas source, such as an anesthesia machine, may be attached. The rear door includes a vent port which is adapted to receive a scavenger or other device for removing carbon dioxide or other gaseous waste from the chamber. The chamber has a first partition wall disposed to slide through one of the side walls adjacent the rear door so that a small animal may enter the chamber through the open rear door and subsequently be confined in the chamber by sliding the first partition wall closed. A second partition wall may be inserted to reduce the size of the chamber. After the animal is sedated, the top cover may be unlatched in order to remove the animal from the chamber and continue anesthesia through conventional routes of administration.

20 Claims, 4 Drawing Sheets

ANESTHESIA INDUCTION CHAMBER FOR SMALL ANIMALS

CROSS-REFERENCE TO RELATED APPLICATION

This application claims the benefit of U.S. Provisional Patent Application Ser. No. 60/141,858, filed Jul. 1, 1999.

BACKGROUND OF THE INVENTION

1. Field of the Invention

The present invention relates to veterinary care devices, and particularly to an anesthesia induction chamber for small animals. The chamber may also be used for the administration of a nebulizer to animals with respiratory problems, for the administration of oxygen to animals in a diabetic coma, as an incubator, or generally for the administration of any form of inhalation therapy for small animals.

2. Description of Related Art

In the practice of veterinary medicine, it is sometimes necessary to administer anesthesia to small animals, such as dogs, cats, birds, guinea pigs, rabbits and the like. The two most common modes of administering anesthesia are by injection or by inhalation. A problem which is frequently encountered in attempting to inject the animal by syringe, in intubating the patient, or in placing an inhalation mask over the animal's mouth is that sick animals are often fractious and occasionally hostile. Consequently, it can be difficult to keep the animal still or immobile while administering the anesthetic.

The present invention provides a substantially enclosed chamber into which small animals requiring anesthesia may be transferred from, e.g., a Hav-A-Hart cage, and sedated so that conventional means for anesthesia maybe employed. The chamber includes substantially gas impermeable walls, an inlet port for the administration of gases, a vent port, a plurality of partition walls, and at least one hinged door. Besides the administration of anesthesia, the chamber is also useful in any situation in which the administration of oxygen or fluids vaporized by a humidifier or nebulizer is desired, such as treatment with humidified oxygen or medications for dilating or clearing the airways. Various patents have been proposed to perform similar functions or which have similar structural elements to the anesthesia induction chamber of the present invention. U.S. Pat. No. 399,609, issued Oct. 13, 1998 to Allen et al., shows a Veterinary Isolation Cage mounted on four legs with a front door having a transparent panel. A pipe exits the top wall of the cage, and a compartment is shown on the bottom of the cage with a second pipe exiting the compartment.

U.S. Pat. No. 275,969, issued Apr. 17, 1889 to T. F. Woodside, describes a wire crate for fowls having a partition wall whose position may be adjusted by an extensible bar engaging a bail attached to the frame of the partition wall. U.S. Pat. No. 3,885,523, issued May 27, 1975 to B. A. Coleman, teaches an enclosed litter box for cats having a partition wall separating a bottom tray into a toilet area and a raised area with a screen floor adjacent the entrance of the box.

U.S. Pat. No. 4,367,696, issued Jan. 11, 1983 to D. P. Hamana, discloses a cat management chamber having fixed side walls, end walls, and a bottom wall. The chamber has a horizontally disposed partition wall forming the top wall of the chamber. The vertical position of the partition wall is adjustable by means of a U-shaped locking pin which extends through holes in one of the side walls and into sleeves on the partition wall. The partition wall has holes for the administration of fluids, and an end wall has a nipple for the administration of anesthesia.

U.S. Pat. No. 4,788,934, issued Dec. 6, 1988 to J. A. Fetter, describes a pet enclosure attached to the exterior wall of a house with a nylon tunnel between a swinging pet door defined in the house door and the entrance of the pet enclosure. U.S. Pat. No. 5,010,845, issued Apr. 30, 1991 to Azpurua et al., shows a reptile cage with a thermostat, infrared light, humidifier, and a divider wall separating areas of the cage. The divider wall hangs from the top edges of the side walls and does not extend entirely to the floor of the cage.

U.S. Pat. No. 4,941,431, issued Jul. 17, 1990 to F. G. Anderson, teaches a system for killing laboratory animals, the animals being placed in an imperforate cage with a wire mesh cover. A device including a cover larger than the cage cover is placed over the cage, a gasket sealing the junction of the device and the cage cover. The device has a quick connect gas inlet fitting and two restricted exhaust ports. A $CO_2$ cylinder with a pressure regulator and a timer valve to deliver a predetermined volume of gas are connected to the quick connect fitting.

United Kingdom Patent No. 2,276,088, published Sep. 21, 1994, discloses an isolator for laboratory animals. When it is desired to introduce items into the isolator, the items are placed into a storage bin below the floor of the isolator. Access to the interior of the isolator is gained through a glove and sleeve in the front wall of the isolator. The door to the storage bin may then be opened and the items brought into the isolator.

A number of patents describe improvements for high density cages for laboratory animals, particular for the delivery of water and air while maintaining environmental separation of the cages to prevent the spread of bacteria and other pathogens between cages. Exemplary patents include: U.S. Pat. No. 4,480,587, issued Nov. 6, 1984 (filter cap for filtering air); U.S. Pat. No. 4,690,100, issued Sep. 1, 1987 (ventilation system with air ducted into the cages); U.S. Pat. No. 4,699,088, issued Oct. 13, 1987 (water manifold for providing water from common source); U.S. Pat. No. 5,190, 879, issued Mar. 2, 1993 to Wolfe, et al. (cages with ultra thin membranes permeable to gases but impermeable to microorganisms); U.S. Pat. No. 5,865,144, issued Feb. 2, 1999 to M. Semenuk (cages with laminated air flow through a perforated bottom); and United Kingdom Patent No. 1,179,551, published Jan. 28, 1970 (air flow system through a cabinet employing multiple filters).

None of the above inventions and patents, taken either singly or in combination, is seen to describe the instant invention as claimed.

SUMMARY OF THE INVENTION

An anesthesia induction chamber for small animals has an enclosed chamber defined by a bottom wall, a pair of opposing side walls, a front end wall, a rear door mounted on a hinge, and a top cover attached to a side wall by an elongated piano hinge. The walls, rear door and top cover are impermeable to gases. The front. end wall has a gas inlet port to which a gas source, such as an anesthesia machine, may be attached. The rear door includes a vent port which is adapted to receive a scavenger or other device for removing carbon dioxide or other gaseous waste from the chamber. The chamber has a first partition wall disposed to slide through one of the side walls adjacent the rear door so that a small animal may enter the chamber through the open rear door and subsequently be confined in the chamber by sliding the first partition wall closed. A second partition wall may be inserted to reduce the size of the chamber. After the animal is sedated, the top cover may be unlatched in order to remove the animal from the chamber and continue anesthesia through conventional routes of administration.

Accordingly, it is a principal object of the invention to provide an anesthesia induction chamber for sedating fractious small animals in order to render the animal more amenable to the administration of anesthesia by conventional routes.

It is another object of the invention to provide a substantially air-tight chamber which small animals may be induced to enter for treatment by inhalation of gases or vaporized medications.

It is a further object of the invention to provide an anesthesia induction chamber for small animals in which a fractious or hostile small animal may be confined after voluntarily entering the chamber by a slidable partition wall which encloses the animal in an air-tight chamber.

Still another object of the invention is to provide an anesthesia induction chamber in which the size of the chamber may be adjusted to suit the size of the animal by insertion of a partition wall into the chamber.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

DETAILED DESCRIPTION OF THE PREFERRED EMBODIMENTS

Figure 1:
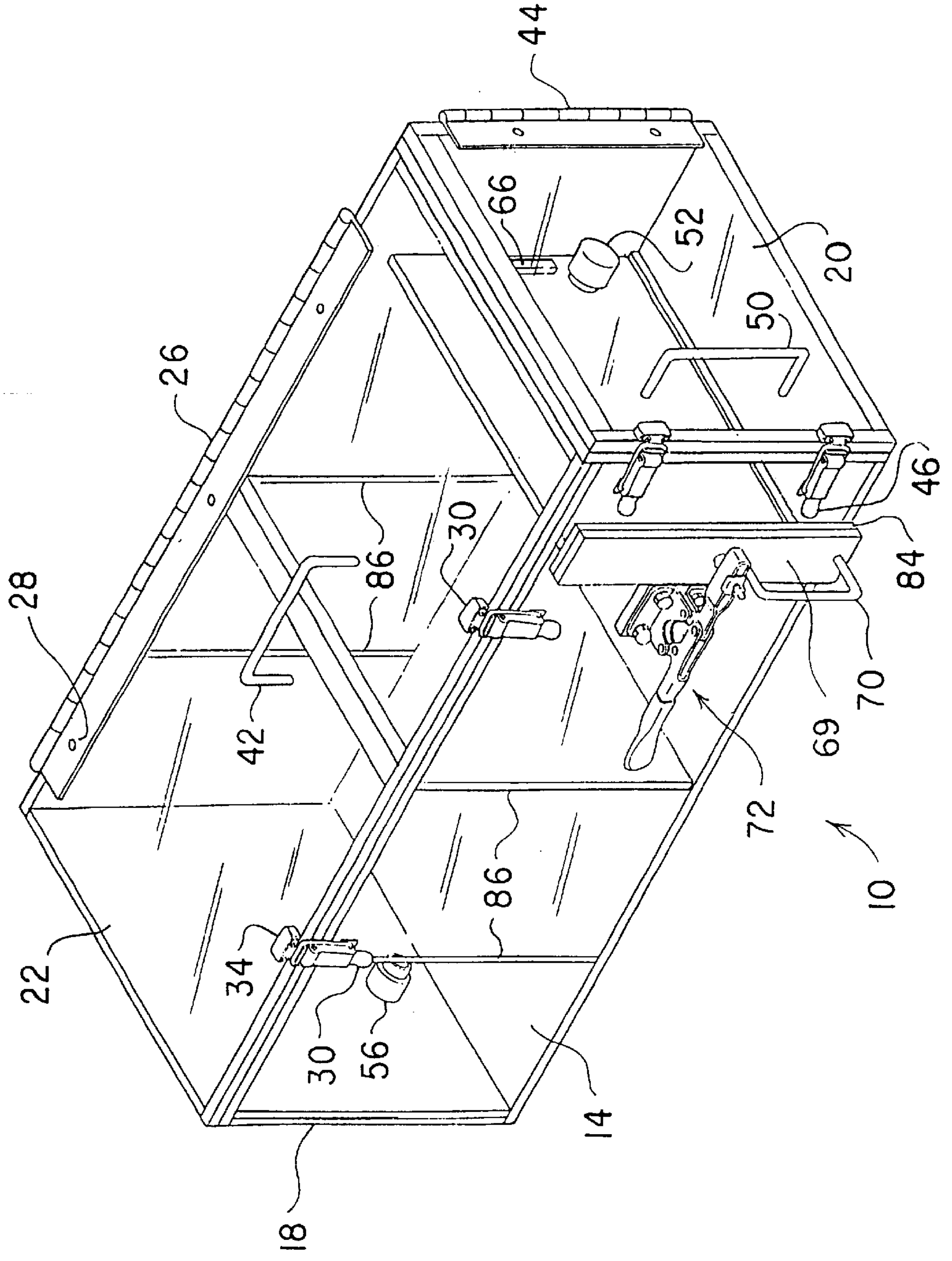
FIG. 1 is a perspective view of an anesthesia induction chamber for small animals according to the present invention.
Figure 2:
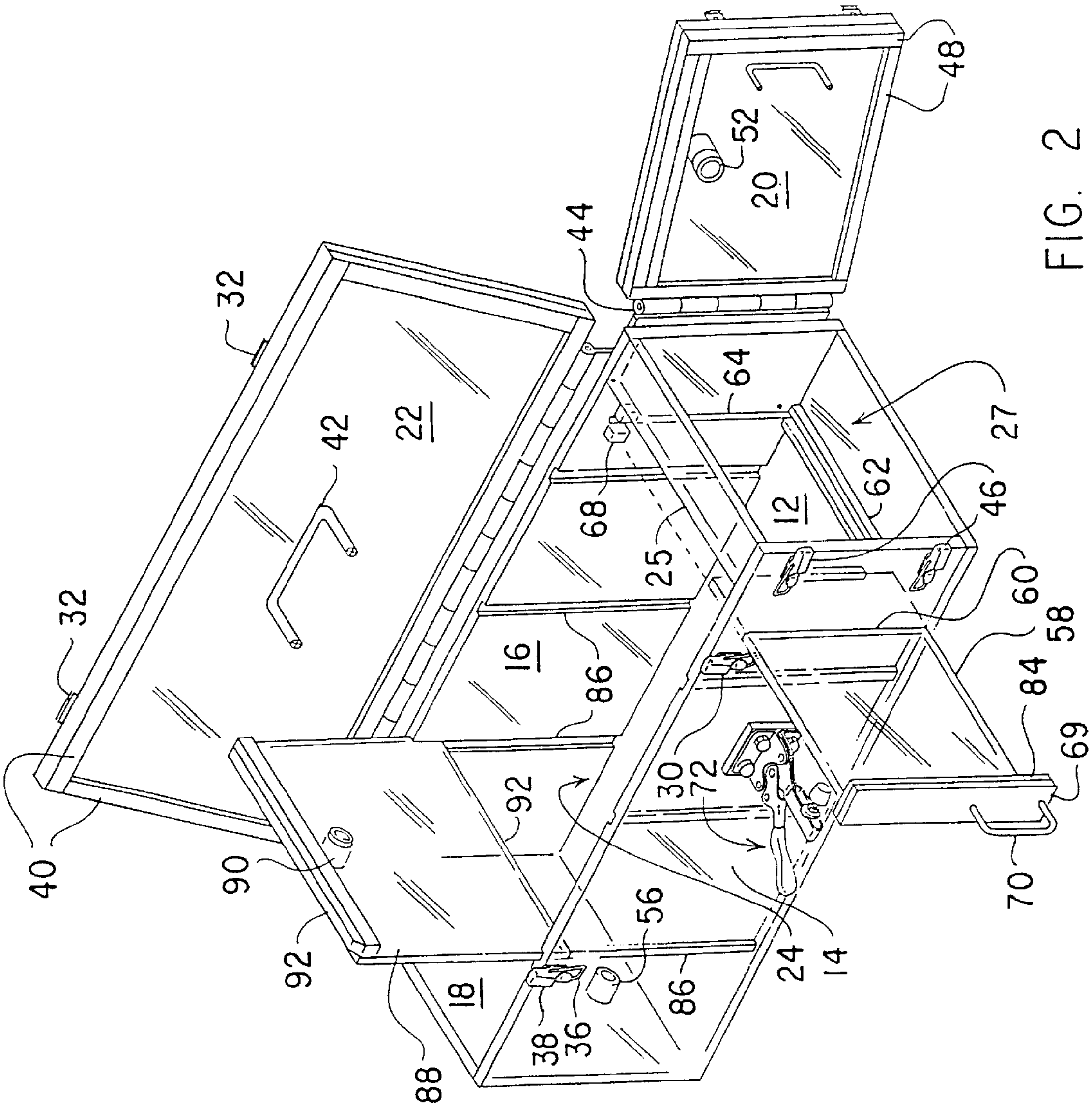
FIG. 2 is a perspective view of the anesthesia induction chamber with the rear door and top covers open and partition walls partially withdrawn.
Figure 3:
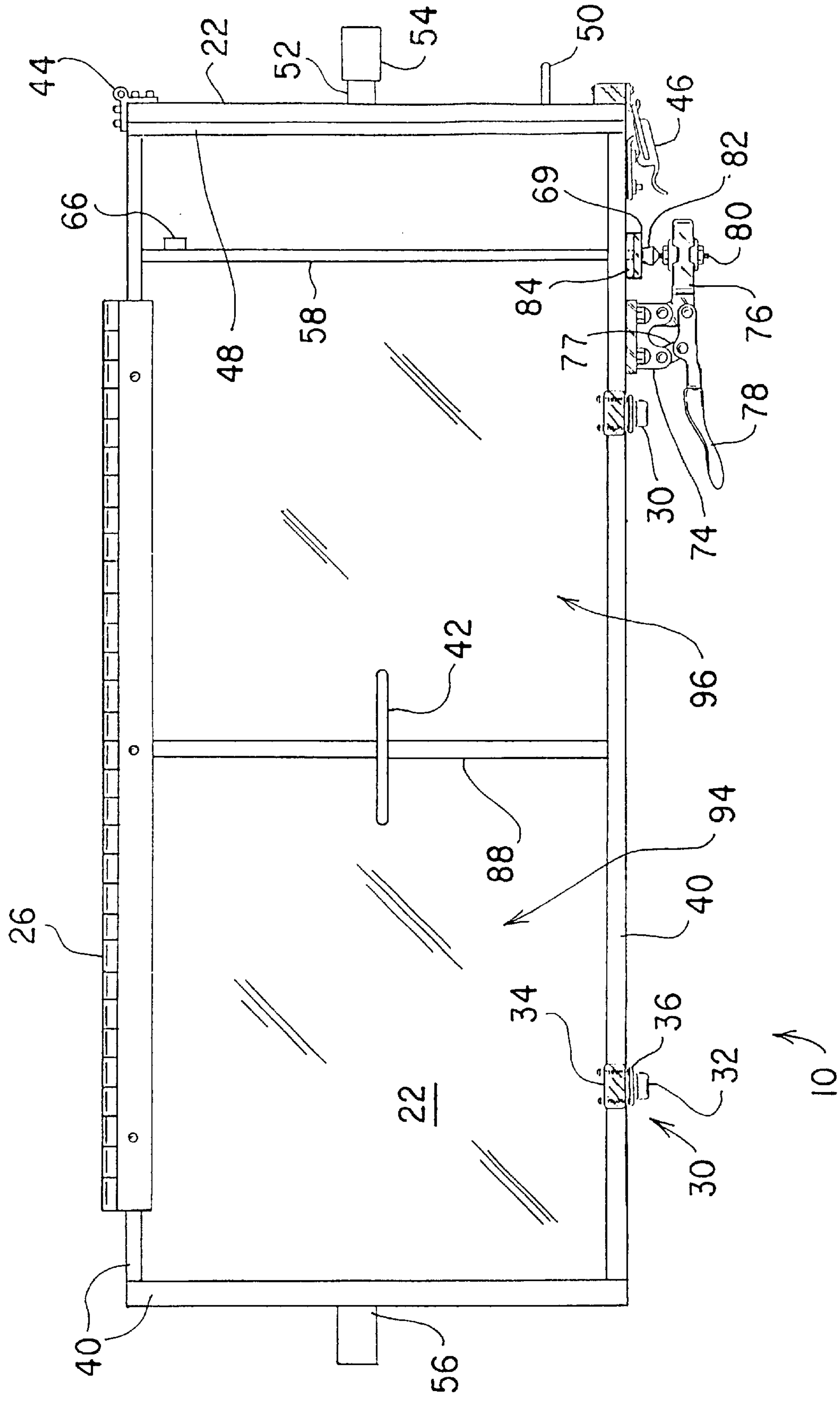
FIG. 3 is a top plan view of the anesthesia induction chamber for small animals according to the present invention.

The present invention is an anesthesia induction chamber for small animals, designated generally as 10 in FIGS. 1 through 3. The chamber 10 has six sides arranged in a rectangular, box configuration, including a bottom wall 12, a first side wall 14, an opposing side wall 16, a front end wall 18, a rear door 20, and a top cover 22. The six sides are made from solid sheets of a rigid, gas impermeable, transparent material, preferably polycarbonate, and define an air-tight enclosed chamber 24. The induction chamber 10 includes a framing strip 25 comprising a rectangular strip of polycarbonate mounted between the top of the side walls 14 and 16 adjacent the rear door 20 and defining a rectangular entrance 27 or opening in combination with the side walls 14, 16 and bottom wall 12.

The top cover 22 is attached to a side wall 16 by an elongated piano hinge 26 secured to the cover 22 and side wall 16 by a plurality of screws and acorn nuts 28 so that the cover 22 may rotate about the hinge 26 through a range of about 270° from a closed position in which the cover 22 is disposed parallel to the bottom wall 12 to an open position in which the cover 22 is disposed parallel to the side wall 16. The cover 22 may be secured in the closed position by latches 30. The particular latches 30 shown in the drawings include hooks 32 mounted on polycarbonate mounting blocks 34 adhesively secured to the cover 22 which are engaged by pivotally mounted loops 36 and latched by a clasp-type lever 38 mounted on the side wall 14. The cover 22 is generally flat and rectangular in shape, and has four strips of a suitable gasket 40 material, such as foam rubber or polyurethane, fixedly attached to the inside surface of the cover 22, as by glue or adhesive, adjacent the four edges of the cover 22, in order to provide an air tight seal between the top cover 22 and the rectangular opening defined by the top edges of the two side walls 14 and 16, the front end wall 18, and the top surface of the framing strip 25. The top cover 22 includes a handle 42 mounted on the exterior surface of the cover 22.

The rear door 20 is pivotally attached to the side wall 16 by a second piano hinge 44 so that the rear door 20 pivots about the hinge 44 through a range of about 270°, between a closed position in which the rear door 20 is disposed perpendicular to the side walls 14 and 16 in order to close the entrance 27, and an open position in which the rear door is disposed parallel to the side wall 16. The induction chamber 10 includes latches 46 attached to the side wall 14, similar in construction to the latches 30, for latching the rear door in the closed position. The rear door 20 is; generally flat and rectangular in shape, and has four strips of a suitable gasket 48 material, such as foam rubber or polyurethane, fixedly attached to the inside surface of the door 20, as by glue or adhesive, adjacent the four edges of the cover 22, in order to provide an air-tight seal for the entrance 27. The rear door 20 has a handle 50 attached to its exterior surface. The rear door 20 includes a vent port 52 formed by a hollow, plastic, cylindrical tube approximately two centimeters in diameter and about three centimeters in length which extends through and projects from the exterior of the rear door 20, and is preferably disposed in the upper half of the door 20. The vent port 52 may be covered by a plastic cap 54 when not in use, as described below.

The front end wall 18 has a gas inlet port 56 formed by a hollow, plastic, cylindrical tube approximately two centimeters in diameter and about three centimeters in length which extends through and projects from the front end wall 18, and is preferably disposed in the lower half of the wall 18.

Preferably, the anesthesia induction chamber 10 includes a first partition wall 58 slidably disposed in the enclosed chamber 24 through a slot 60 defined vertically in a side wall 14. The first partition wall 58 is disposed parallel to and adjacent the rear door 20. The partition wall 58 is guided by a pair of elongated, narrow rectangular guide strips 62 adhesively attached to the bottom wall 12 of the chamber 10 in parallel relation, spaced apart by a distance slightly greater than the thickness of the partition wall 58. The edge of the partition wall 58 facing the interior of the enclosed chamber 24 slides into a groove 64 routed into the polycarbonate side wall 16, the groove having a width slightly greater than the thickness of the partition wall 58. A pair of guide blocks 68 are adhesively secured to the side wall 16 on opposing sides of the groove 64 in order to channel the partition wall 58 into the groove 64.

The partition wall 58 has a stop block 66 adhesively secured to a face of the wall 58 so that the partition wall may not be completely removed from the enclosed chamber 24 through the slot 60. The height of the partition wall 58 and the slot 60 are less than the height of the side walls 14 and 16 in order to leave a gap of slightly more than one centimeter between the top of the partition wall 58 and the top cover 22 so that gases in the enclosed chamber 24 may flow over the partition wall 58 to the vent: port 52 in the rear door 20.

The exterior edge of the partition wall 58 is mounted to a rectangular transverse block 69 of polycarbonate disposed perpendicular to the partition wall 58 on the exterior of the induction chamber 10, so that the partition wall 58 bisects the block 69. The block 69 has a handle 70 mounted on its exterior surface to aide in sliding the partition wall 58 through the slot 60. The induction chamber 10 has a toggle clamp 72 mounted on the exterior of the side wall 14 adjacent the slot 60. The toggle clamp 72 may be, for example, a De-Sta-Co® clamp, model number 215-U, made by Delaware Capital Formation, Inc. of Wilmington, Del.

As shown in FIG. 3, the clamp 72 has a mounting bracket 74, which is secured to the side wall 14 by a plurality of screws and acorn nuts, a clamp arm 76 pivotally attached to the mounting bracket 74, and a clamp handle 78 which is pivotally attached to the clamp arm 76, and is also pivotally attached to the mounting bracket 74 by a short link 77. The clamp arm 76 includes an adjustable stud 80 having a cushioned foam stopper 82 at the end which is applied to the surface to be clamped.

As shown in FIGS. 1 and 3, when the partition wall 58 is slidably disposed within the enclosed chamber 24, toggle clamp 72 may be latched in a closed position with the clamp handle 78 disposed parallel to the side wall 14 and the stopper 82 applying pressure to the block 69 in order to clamp the block 69 against the side wall 14. The block 69 has a pair of strips of a suitable gasket 84 material, such as foam rubber or polyurethane, fixedly attached to the inside surface of the block 69 on both sides of the partition wall 58 in order to provide an air-tight seal about the opening of the slot 60 when the toggle clamp 72 is in the closed position. As shown in FIG. 2, in the open position the clamp handle 72 is disposed substantially perpendicular to the side wall 14 so that the partition wall 58 may be withdrawn from the enclosed chamber 24 through the slot 60 until the stop block 66 engages the side wall 14.

The anesthesia induction chamber 10 may include a plurality of grooves 86 defined in the opposing side walls 14 and 16. A second partition wall 88 may be slidably disposed in a pair of the grooves 86, as shown in FIGS. 2 and 3, by insertion into the grooves 86 vertically, the top cover 22 being opened. The grooves 86 may easily be defined in polycarbonate walls with a router. The second partition wall 88 may be used to reduce the volume of the enclosed chamber 24 when anesthetizing very small animals, or it may be used to divide the enclosed chamber 24 into two chambers 94 and 96 for anesthetizing two animals simultaneously. The second partition wall 88 may have a port 90 defined therein to provide fluid communication between the two chambers 94 and 96, or the height of the second partition wall may be less than the height of the opposing side walls 14 and 16 so that gases may diffuse between the adjacent chambers 94 and 96. The second partition wall 88 may include appropriate gasket material 92 on the bottom edge of the wall 88, and optionally on the top edge of the wall 88 if the wall 88 extends to the full height of the side walls 14 and 16.

The first 58 and second 88 partition walls are preferably made from a solid, transparent material, such as polycarbonate.

In use, the top cover 22 is latched closed and the rear door 20 is opened about the hinge 44, the toggle clamp 72 being in the open position and the first partition wall 58 being withdrawn from the enclosed chamber 24 to the limit permitted by the stop block 66. The patient is introduced into the chamber 24. If the patient is a fractious or hostile small animal housed in a Hav-A-Hart cage., the cage is butted up against the entrance 27 and the animal is, induced to enter the enclosed chamber 27. Once the patient advances past the plane of the first partition wall 58, the chamber 24 is enclosed by sliding the wall 58 through the slot and closing the toggle clamp 72 to seal the enclosed chamber 24. The rear door 20 is then closed and latched. A scavenger (not shown) containing charcoal, a barium compound, or other suitable filter media may be attached to the vent port 52 to remove carbon dioxide and other waste gases from the enclosed chamber 24. An anesthesia machine (not shown) for administering an appropriate anesthetic gas, such as isoflurane, and withdrawing carbon dioxide, may be connected to the gas inlet 56, using a Y-connector or other appropriate tubing, as is known in the art. Anesthesia is administered until the patient is sufficiently sedated, usually about ten minutes, at which time the patient may be removed from the induction chamber 10 by opening the top cover 22. The patient may then be intubated or further anesthetized by injection.

The anesthesia induction chamber 10 may be used alternatively for respiratory therapy by connecting an oxygen source or a nebulizer with vaporized medication to the gas inlet port 56 in lieu of the anesthesia machine.

Figure 4:
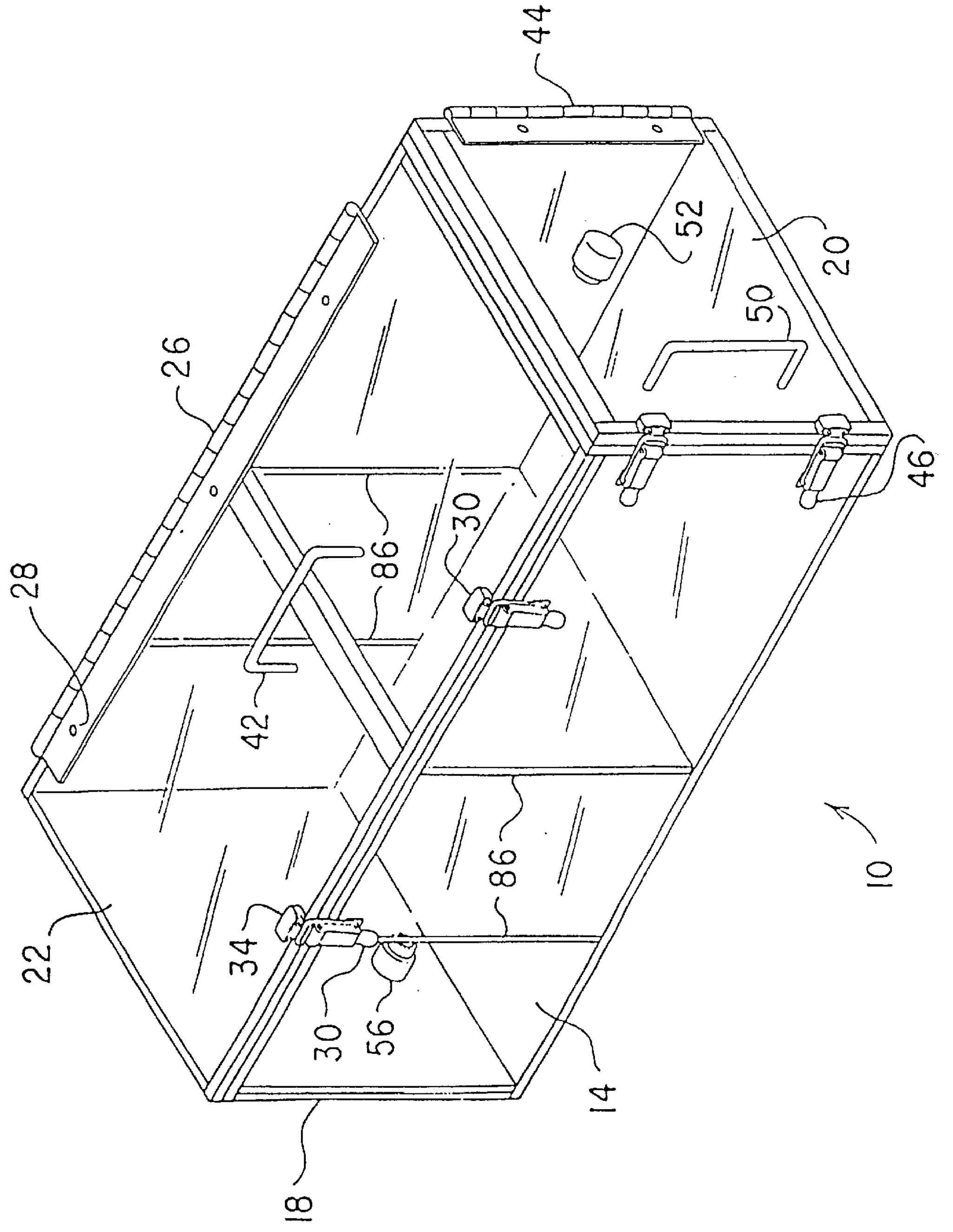
FIG. 4 is a perspective view of an alternative embodiment of an anesthesia induction chamber for small animals according to the present invention. Similar reference characters denote corresponding features consistently throughout the attached drawings.

In an alternative embodiment, shown in FIG. 4, the anesthesia chamber 10 need not include the partition wall 58. Since there is no partition wall 58 slidable though the side wall 14, there is; also no need for the clamp 72. The remaining structure of this; alternative embodiment is the same as the first embodiment of the anesthesia induction chamber 10 described above and will not be described further. This embodiment is a more economical version of the anesthesia chamber 10 which is quite useful in the treatment of more docile and easily controlled small animals.

It is to be understood that the present invention is not limited to the sole embodiments described above, but encompasses any and all embodiments within the scope of the following claims.

I claim:

1. An anesthesia induction chamber for small animals, comprising a box-shaped, air-tight, enclosed chamber defined by:

a) a bottom wall;

b) a first side wall having a slot defined vertically therein;

c) a second side wall opposing said first side wall;

d) a front end wall having a gas inlet port extending through and projecting from the front end wall;

e) a rear door pivotally attached to said second side wall and having a vent port extending through and projecting from the rear door; and f) a top cover pivotally mounted to said second side wall;

said anesthesia induction chamber further comprising a first partition wall slidably disposed through the slot defined in said first side wall adjacent to said rear door.

2. The anesthesia induction chamber according to claim 1, wherein said bottom wall, said first side wall, said second side wall, said front end wall, said rear door, said top cover, and said first partition wall are made from solid sheets of a rigid, gas impermeable, transparent material.

3. The anesthesia induction chamber according to claim 1, wherein said bottom wall, said first side wall, said second side wall, said front end wall, said rear door, said top cover, and said first partition wall are made from polycarbonate.

4. The anesthesia induction chamber according to claim 1, further comprising a transverse block attached to an exterior edge of said first partition wall, said transverse block being perpendicular to and bisected by said first partition wall, said transverse block being disposed outside of said chamber.

5. The anesthesia induction chamber according to claim 4, further comprising a handle attached to an exterior surface of said transverse block.

6. The anesthesia induction chamber according to claim 4, further comprising a clamp attached to said first side wall, said clamp having a closed position in which said transverse block is clamped against said first side wall so that said first partition wall is disposed entirely within said enclosed chamber parallel to said rear door, and an open position in which said first partition wall may be at least partially withdrawn from said enclosed chamber through the slot defined in said first side wall.

7. The anesthesia induction chamber according to claim 6, wherein said transverse block further comprises an interior surface facing said first side wall, and wherein said transverse block further comprises a plurality of gaskets fixedly attached to the interior surface of said transverse block in order to form an air-tight seal against the slot defined in said first wall when said clamp is in the closed position.

8. The anesthesia induction chamber according to claim 1, further comprising:

a) a groove defined vertically in said second side wall opposite the slot defined in said first side wall;

b) a pair of guide strips fixedly attached to said bottom wall, said guide strips being spaced apart a distance slightly greater than a thickness of said first partition wall; and c) a pair of guide blocks fixedly attached to said second side wall on opposite sides of said groove, said guide strips and said guide blocks channeling an edge of said first partition wall into said groove when said first partition wall slides into said enclosed chamber.

9. The anesthesia induction chamber according to claim 1, wherein said first partition wall further comprises a stop block attached to a surface of said first partition wall, said stop block preventing said first partition wall from sliding entirely out of said enclosed chamber.

10. The anesthesia induction chamber according to claim 1, wherein said top cover is attached to said second side wall by an elongated piano hinge, so that said top cover pivots from a closed position in which said top cover is disposed parallel to said bottom wall through a range of about 270° to an open position in which said top cover is disposed substantially parallel to said second side wall.

11. The anesthesia induction chamber according to claim 10, further comprising a plurality of latches mounted on said first side wall having pivotally mounted loops which engage a plurality of hooks mounted on said top cover, said latches being secured by a clasp lever.

12. The anesthesia induction chamber according to claim 10, wherein said top cover has an inside surface, said anesthesia induction chamber further comprising a plurality of gaskets attached to the inside surface of said top cover in order to form an air-tight seal when said cover is latched in a closed position.

13. The anesthesia induction chamber according to claim 1, wherein said rear door is attached to said second side wall by a piano hinge, so that said rear door pivots from a closed position in which said rear door is disposed parallel to said front end wall through a range of about 270° to an open position in which said rear door is disposed substantially parallel to said second side wall.

14. The anesthesia induction chamber according to claim 13, further comprising a plurality of latches mounted on said first side wall having pivotally mounted loops which engage a plurality of hooks mounted on said rear door, said latches being secured by a clasp lever.

15. The anesthesia induction chamber according to claim 13, wherein said rear door has an inside surface, said anesthesia induction chamber further comprising a plurality of gaskets attached to the inside surface of said rear door in order to form an air-tight seal when said door is latched in a closed position.

16. The anesthesia induction chamber according to claim 1, wherein said first side wall and said second side wall each have a plurality of grooves defined vertically therein, each groove in said first side wall being in registry with a groove in said second wall, said anesthesia induction chamber further comprising a second partition wall slidable in the grooves defined in said first side wall and said second side wall in order to divide said enclosed chamber into a first enclosed chamber and a second enclosed chamber.

17. The anesthesia induction chamber according to claim 16, further comprising a port defined in said second partition wall, whereby said first enclosed chamber and said second enclosed chamber are in fluid communication.

18. The anesthesia induction chamber according to claim 16, wherein said second partition wall has a height less than the height of said first side wall and said second side wall, defining a gap between a top edge of said second partition wall and said top cover, whereby said first enclosed chamber and said second enclosed chamber are in fluid communication.

19. An anesthesia induction chamber for small animals, comprising a box-shaped, air-tight, enclosed chamber defined by:

a) a bottom wall;

b) a first side wall attached to said bottom wall;

c) a second side wall opposing said first side wall;

d) a front end wall having a gas inlet port extending through and projecting from the front end wall;

e) a rear door pivotally attached to said second side wall and having a vent port extending through and projecting from the rear door;

f) a top cover pivotally mounted to said second side wall;

g) a pair of piano hinges, one of said hinges attaching said rear door to said second side wall and the other of said hinges attaching said top cover to said second wall, said hinges permitting said rear door and said top cover to pivot about 270° between an open position and a closed position;

h) first latching means for latching said rear door in the closed position and second latching means for latching said top cover in the closed position;

i) a plurality of gaskets disposed on said rear door and on said top cover in order to form an air-tight seal when said rear door and said top cover are latched in the closed position; and k) wherein said bottom wall, said first side wall, said second side wall, said front end wall, said rear door, and said top cover are made from transparent polycarbonate.

20. The anesthesia induction chamber according to claim 19, wherein said first side wall and said second side wall each have a plurality of grooves defined vertically therein, each groove in said first side wall being in registry with a groove in said second wall, said anesthesia induction chamber further comprising a second partition wall slidable in the grooves defined in said first side wall and said second side wall in order to divide said enclosed chamber into a first enclosed chamber and a second enclosed chamber.

* * * * *